United States Patent
Takahashi et al.

(10) Patent No.: US 12,368,812 B2
(45) Date of Patent: Jul. 22, 2025

(54) IMAGE DISPLAY SYSTEM AND IMAGE DISPLAY METHOD

(71) Applicant: DIC Corporation, Tokyo (JP)

(72) Inventors: Masato Takahashi, Tokyo (JP); Yasuhiro Morihara, Tokyo (JP); Norimichi Tsumura, Chiba (JP); Ryo Takahashi, Chiba (JP); Keiko Ogawa, Ishikawa (JP); Isseki Kin, Tokyo (JP)

(73) Assignee: DIC Corporation, Tokyo (JP)

( * ) Notice: Subject to any disclaimer, the term of this patent is extended or adjusted under 35 U.S.C. 154(b) by 411 days.

(21) Appl. No.: 18/010,908

(22) PCT Filed: Jun. 15, 2021

(86) PCT No.: PCT/JP2021/022642
§ 371 (c)(1),
(2) Date: Dec. 16, 2022

(87) PCT Pub. No.: WO2021/256459
PCT Pub. Date: Dec. 23, 2021

(65) Prior Publication Data
US 2023/0239419 A1    Jul. 27, 2023

(30) Foreign Application Priority Data

Jun. 17, 2020  (JP) ................................ 2020-104693
Mar. 11, 2021  (JP) ................................ 2021-039227

(51) Int. Cl.
*H04N 1/60*   (2006.01)
*G06T 7/11*   (2017.01)
*G06T 7/90*   (2017.01)
(Continued)

(52) U.S. Cl.
CPC ................ *H04N 1/60* (2013.01); *G06T 7/11* (2017.01); *G06T 7/90* (2017.01); *G06V 10/60* (2022.01);
(Continued)

(58) Field of Classification Search
CPC .... H04N 1/60; H04N 9/73; G06T 7/11; G06T 7/90; G06T 2207/10024;
(Continued)

(56) References Cited

U.S. PATENT DOCUMENTS 6,707,579 B1    3/2004  Komiya et al.
2014/0148708 A1    5/2014  Cosentino et al.
(Continued)

FOREIGN PATENT DOCUMENTS

CN    101947101 A    1/2011
CN    103340598 A    10/2013
(Continued)

OTHER PUBLICATIONS

Francisco Hideki Imai et al., "Principal Component Analysis of Skin Color and Its Application to Colorimetric Color Reproduction on CRT Display and Hardcopy" Journal of Imaging Science and Technology, vol. 40, No. 5, Sep. 1, 1996, pp. 422-430 (9 pages).
(Continued)

*Primary Examiner* — Quang N Vo
(74) *Attorney, Agent, or Firm* — Osha Bergman Watanabe & Burton LLP

(57) ABSTRACT

An object of the invention is to provide an image display system and the like useful for a remote diagnosis and treatment using color information such as a skin color and a tongue color of a patient. There is provided an image display system including: a color chart including a plurality of patches that include at least three patches selected from a group consisting of first to seventh patches having specific colors; an imaging device configured to simultaneously image the color chart and a person to be imaged and acquire image data; and a display device configured to receive the image data and display the image data as an image on a display unit.

12 Claims, 3 Drawing Sheets

(51) Int. Cl.
*G06V 10/60* (2022.01)
*G06V 10/74* (2022.01)
*G09G 5/06* (2006.01)
*H04N 9/73* (2023.01)

(52) U.S. Cl.
CPC .............. *G06V 10/761* (2022.01); *G09G 5/06* (2013.01); *H04N 9/73* (2013.01); *G06T 2207/10024* (2013.01); *G06T 2207/30196* (2013.01)

(58) Field of Classification Search
CPC ........ G06T 2207/30196; G06V 10/761; G06V 10/60; G09G 5/06
See application file for complete search history.

(56) References Cited

U.S. PATENT DOCUMENTS

2017/0314994 A1* 11/2017 Tanimura ................. H04N 1/60
2019/0122395 A1* 4/2019 Fukasawa ................. G06T 7/90

FOREIGN PATENT DOCUMENTS

| | | |
|---|---|---|
| CN | 110495888 A | 11/2019 |
| CN | 110739047 A | 1/2020 |
| JP | H10-165375 A | 6/1998 |
| JP | 2000-52571 A | 2/2000 |
| JP | 2003-134526 A | 5/2003 |
| JP | 2008-22410 A | 1/2008 |
| JP | 2011-212013 A | 10/2011 |
| JP | 2018-120184 A | 8/2018 |
| KR | 10-2013-0067657 A | 6/2013 |

OTHER PUBLICATIONS

Trisha Greenhalgh et al., "Video consultations: a guide for practice", BJGP Life, 2020 (9 pages).

Futa Matsushita et al., "Evaluation of Kampo disease states using facial images", Artificial Life and Robotics, 2019, 24:44-51 (8 pages).

* cited by examiner

IMAGE DISPLAY SYSTEM AND IMAGE DISPLAY METHOD

TECHNICAL FIELD

The present invention relates to an image display system and an image display method.

BACKGROUND ART

A market related to a remote medical care is growing, partly chronic disease treatment, mobile health apps, and the like. Due to spread of novel coronavirus infection (COVID-19), importance of the remote diagnosis and treatment is also recognized from a viewpoint of infection prevention, and it is necessary to construct a good remote diagnosis and treatment system.

A person infected with the novel coronavirus may infect another person with the novel coronavirus before COVID-19 symptoms appear. Therefore, in the spread of COVID-19, it is necessary to provide a diagnosis and treatment based on an assumption of the infection in a normal face-to-face diagnosis and treatment.

Generally, the face-to-face diagnosis and treatment is performed based on biochemical examination results of collected blood, but it is necessary to take into consideration a risk of infection during blood collection. In addition, since it takes a long time to recover from COVID-19, infected individuals need to be quarantined for at least two weeks. When the number of patients rapidly increases, hospitals run out of beds, and patients with asymptomatic infection or mild symptoms are quarantined at homes, hotels, or other unsupervised locations, and thus care of these patients is also covered by the remote diagnosis and treatment.

In order to address these situations, Greenhalgh et al. disclose a guide for general practitioners in charge of primary care (see NTL 1). This guide states that, pulse wave measurement with a fitness equipment may not be suitable for grasping a state of a patient from a viewpoint of reliability. Further, a general physical evaluation such as a skin color or the like of a person is mentioned, but variations in color appearance are not sufficiently described.

Here, the remote diagnosis and treatment is performed not only by consultation through a telephone or the like, but also by a diagnostician such as a doctor observing a patient using an information communication system such as a conference system capable of transmitting and receiving images.

In the diagnosis and treatment, a diagnosis and treatment in which importance is placed on a color may be performed. For example, observation of a gum color in dentistry, observation of a skin color in dermatology, observation of a throat color in otorhinolaryngology, diagnosis (inspection) by a skin color, a tongue color, and the like performed in Chinese medicine. In this type of diagnosis and treatment, inaccurate color recognition may affect the diagnosis.

Therefore, when this type of diagnosis and treatment is performed in a manner of the remote diagnosis and treatment, it is important to accurately recognize the colors.

A practical color reproduction system is standardized by the International Commission on Illumination (CIE). However, when color reproduction is actually performed, it is not easy because use of a calibration equipment or the like is required. In a case of performing the color reproduction in the remote medical care, correction of a display on a doctor side can be relatively easily performed by using a profile creation tool of a commercially available display device. However, correction on a patient side requires correction in consideration of a spectral radiant intensity of a light source and a camera performance, and is not easy. In addition, due to recent advances in techniques, smartphones perform automatic color correction, such as, not only auto white balance, but also skin beautifying effects, making the correction even more difficult.

On the other hand, in the remote diagnosis and treatment, in order to make a more accurate diagnosis by quantifying objective biological information obtained from skin colors such as a facial skin color without being affected by the image color reproduction of the display, a diagnosis system that displays images of various diagnosable objects is proposed (see PTL 1). The diagnosis system includes an imaging device that captures an image of an object as image data quantified for each pixel, a calculation device that obtains predetermined data necessary for various diagnoses from the image data, a transfer device that transfers any one of the image data obtained by the imaging device and the predetermined data and the image data, and a display device that displays the predetermined data and the image data. However, according to this proposed technique, the diagnosis system is complicated and lacks in simplicity.

CITATION LIST

Patent Literature

PTL 1: JPH10-165375A

Non Patent Literature

NTL 1: Trisha Greenhalgh et. al., Video consultations: a guide for practice, BJGP Life (2020)

SUMMARY OF INVENTION

Technical Problem

Therefore, inventors of the invention studied techniques useful in performing a diagnosis and treatment by a doctor who places importance on colors and a diagnosis and treatment by dentist who uses colors through the remote diagnosis and treatment, including the diagnoses (inspections) based on the skin color, the tongue color, and the like performed in Chinese medicine.

That is, an object of the invention is to provide an image display system and an image display method which are useful for a remote diagnosis and treatment using color information such as a skin color and a tongue color of a patient.

Solution to Problem

As a result of intensive studies to solve the above problems, the inventors found that it is possible to easily perform the remote diagnosis and treatment using color information such as the skin color and the tongue color of the patient by simultaneously imaging a color chart including the color information such as the skin color and the tongue color at the time of imaging the patient, and made the invention.

That is, the invention includes the following aspects.

[1] An image display system includes:

a color chart including a plurality of patches that include at least three patches selected from a group consisting of the following first to seventh patches;

an imaging device configured to simultaneously image the color chart and a person to be imaged and acquire image data; and a display device configured to receive the image data and display the image data as an image on a display unit thereof.

The first patch includes a region that has a first color represented by L*a*b* values in which L*=72, a*=8, and b*=22 or has a color having a color difference ΔE* of 5 or less in a L*a*b* color space with respect to the first color, the second patch includes a region that has a second color represented by the L*a*b* values in which L*=78, a*=30, and b*=15 or has a color having a color difference ΔE* of 5 or less in the L*a*b* color space with respect to the second color, the third patch includes a region that has a third color represented by the L*a*b* values in which L*=58, a*=27, and b*=7 or has a color having a color difference ΔE* of 5 or less in the L*a*b* color space with respect to the third color, the fourth patch includes a region that has a fourth color represented by the L*a*b* values in which L*=60, a*=20, and b*=5 or has a color having a color difference ΔE* of 5 or less in the L*a*b* color space with respect to the fourth color, the fifth patch includes a region that has a fifth color represented by the L*a*b* values in which L*=48, a*=25, and b*=2 or has a color having a color difference ΔE* of 5 or less in the L*a*b* color space with respect to the fifth color, the sixth patch includes a region that has a sixth color represented by the L*a*b* values in which L*=52, a*=50, and b*=13 or has a color having a color difference ΔE* of 5 or less in the L*a*b* color space with respect to the sixth color, and the seventh patch includes a region that has a seventh color represented by the L*a*b* values in which L*=33, a*=40, and b*=30 or has a color having a color difference ΔE* of 5 or less in the L*a*b* color space with respect to the seventh color.

[2] In the image display system according to [1], the plurality of patches include a plurality of achromatic color patches having different brightness.

[3] In the image display system according to [1] or [2], the plurality of patches include a plurality of chromatic color patches whose colors are different from the first color to the seventh color.

[4] In the image display system according to any one of [1] to [3], the color chart has an area of 40 cm$^2$ or more and 150 cm$^2$ or less.

[5] In the image display system according to any one of [1] to [4], each of the plurality of patches has an area of 0.25 cm$^2$ or more and 4 cm$^2$ or less.

[6] In the image display system according to any one of [1] to [5], the color chart includes an automatic recognition marker for automatically recognizing at least one of the plurality of patches.

[7] In the image display system according to any one of [1] to [6], the color chart has a blank portion at a lower right portion on a main surface thereof.

[8] In the image display system according to any one of [1] to [7], the imaging device is an electronic device having a camera function.

[9] In the image display system according to any one of [1] to [8], the display device is a personal computer.

[10] In the image display system according to any one of [1] to [9], the display device further includes a color correction unit configured to correct a display color of the display unit and color information of the image data such that a color of at least one patch of the color chart in the image displayed on the display unit approaches or matches a color of at least one corresponding patch of a color chart measured under a light source at a place where the display unit is placed.

[11] In the image display system according to [10], the color correction unit includes a first correction unit configured to correct the display color of the display unit such that a color of at least one patch of the color chart measured under the light source at the place where the display unit is placed and a corresponding display color of the display unit approach or match each other, and a second correction unit configured to correct the color information of the image data such that a color of at least one patch of the color chart measured under the light source at the place where the display unit is placed and a color of at least one corresponding patch of the color chart in the image data approach or match each other.

[12] An image display method includes:

simultaneously imaging a color chart including a plurality of patches that include at least three patches selected from a group consisting of the following first to seventh patches, and a person to be imaged, and acquiring image data; and receiving the image data and displaying the image data as an image on a display unit.

The first patch includes a region that has a first color represented by L*a*b* values in which L*=72, a*=8, and b*=22 or has a color having a color difference ΔE* of 5 or less in a L*a*b* color space with respect to the first color, the second patch includes a region that has a second color represented by the L*a*b* values in which L*=78, a*=30, and b*=15 or has a color having a color difference ΔE* of 5 or less in the L*a*b* color space with respect to the second color, the third patch includes a region that has a third color represented by the L*a*b* values in which L*=58, a*=27, and b*=7 or has a color having a color difference ΔE* of 5 or less in the L*a*b* color space with respect to the third color, the fourth patch includes a region that has a fourth color represented by the L*a*b* values in which L*=60, a*=20, and b*=5 or has a color having a color difference ΔE* of 5 or less in the L*a*b* color space with respect to the fourth color, the fifth patch includes a region that has a fifth color represented by the L*a*b* values in which L*=48, a*=25, and b*=2 or has a color having a color difference ΔE* of 5 or less in the L*a*b* color space with respect to the fifth color, the sixth patch includes a region that has a sixth color represented by the L*a*b* values in which L*=52, a*=50, and b*=13 or has a color having a color difference ΔE* of 5 or less in the L*a*b* color space with respect to the sixth color, and the seventh patch includes a region that has a seventh color represented by the L*a*b* values in which L*=33, a*=40, and b*=30 or has a color having a color difference ΔE* of 5 or less in the L*a*b* color space with respect to the seventh color.

Advantageous Effects of Invention

According to the invention, it is possible to provide an image display system and an image display method which are useful for a remote diagnosis and treatment using color information such as a skin color and a tongue color of a patient.

DESCRIPTION OF EMBODIMENTS

Hereinafter, an image display system and an image display method of the invention will be described in detail, but the description regarding constituent elements described below is an example of an embodiment of the invention, and the invention is not limited to these contents.
(Image Display System and Image Display Method)

The image display system of the invention includes at least a color chart, an imaging device, and a display device, and further includes other devices as necessary.

The image display method of the invention includes at least an imaging step and a display step, and further includes other steps as necessary.

Figure 1:
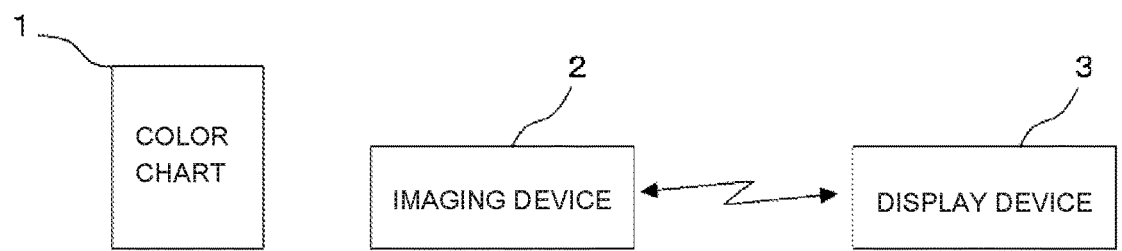
FIG. 1 is a configuration diagram of an example of an image display system.

FIG. 1 is a configuration diagram of an example of the image display system. The image display system in FIG. 1 includes a color chart 1, an imaging device 2, and a display device 3.
<Color Chart>

The color chart includes a plurality of patches.

The plurality of patches include at least three patches selected from the group consisting of the following first patch to seventh patch.

First patch: a region that has a first color represented by $L^*a^*b^*$ values in which $L^*=72$, $a^*=8$, and $b^*=22$ or has a color having a color difference $\Delta E^*$ of 5 or less in a $L^*a^*b^*$ color space with respect to the first color Second patch: a region that has a second color represented by the $L^*a^*b^*$ values in which $L^*=78$, $a^*=30$, and $b^*=15$ or has a color having a color difference $\Delta E^*$ of 5 or less in the $L^*a^*b^*$ color space with respect to the second color Third patch: a region that has a third color represented by the $L^*a^*b^*$ values in which $L^*=58$, $a^*=27$, and $b^*=7$ or has a color having a color difference $\Delta E^*$ of 5 or less in the $L^*a^*b^*$ color space with respect to the third color Fourth patch: a region that has a fourth color represented by the $L^*a^*b^*$ values in which $L^*=60$, $a^*=20$, and $b^*=5$ or has a color having a color difference $\Delta E^*$ of 5 or less in the $L^*a^*b^*$ color space with respect to the fourth color Fifth patch: a region that has a fifth color represented by the $L^*a^*b^*$ values in which $L^*=48$, $a^*=25$, and $b^*=2$ or has a color having a color difference $\Delta E^*$ of 5 or less in the $L^*a^*b^*$ color space with respect to the fifth color Sixth patch: a region that has a sixth color represented by the $L^*a^*b^*$ values in which $L^*=52$, $a^*=50$, and $b^*=13$ or has a color having a color difference $\Delta E^*$ of 5 or less in the $L^*a^*b^*$ color space with respect to the sixth color Seventh patch: a region that has a seventh color represented by the $L^*a^*b^*$ values in which $L^*=33$, $a^*=40$, and $b^*=30$ or has a color having a color difference $\Delta E^*$ of 5 or less in the $L^*a^*b^*$ color space with respect to the seventh color The color of the first patch corresponds to a color of tongue coating formed due to accumulation of moisture (excess water).

The color of the second patch corresponds to a skin color that indicates an inflammation.

The color of the third patch corresponds to a color of a tongue having blood stasis (poor microcirculation).

The color of the fourth patch corresponds to a color of a portion of a tongue covered with healthy tongue coating.

The color of the fifth patch corresponds to a color of deep lingual vein in an engorgement state=a blood stasis state.

The color of the sixth patch corresponds to a color of a healthy tongue.

The color of the seventh patch corresponds to a color of a tongue having heat.

By using the color chart having at least three patches selected from the group consisting of the first patch to the seventh patch, it is possible to easily perform a diagnosis using color information such as a skin color and a tongue color of a patient.

The color chart includes at least three patches selected from the group consisting of the first patch to the seventh patch, preferably includes at least five patches, and more preferably includes seven patches.

A combination of the first patch to the seventh patch is not particularly limited as long as it is a combination of three or more patches selected from the seven patches, and it is preferable to select three or more patches having different color tones such as purplish-red, pale red-purple, and deep yellow-red.

The color chart may include patches other than the first patch to the seventh patch. Such patches include an achromatic patch and a chromatic patch.

The plurality of patches include, for example, a plurality of achromatic color patches having different brightness. The number of types of the achromatic color patches is, for example, five to seven. In a case where the number of types of the achromatic color patches is three or less, for example, when color correction for an image with the color chart imaged by a camera is performed using the achromatic color patches, non-linearity of the camera is not sufficiently coped with, and the accuracy of the color correction may decrease. In this regard, the number of types of the achromatic color patches is preferably five or more.

The plurality of patches include, for example, a plurality of chromatic color patches whose colors are different from the first color to the seventh color. The number of types of these chromatic color patches is, for example, 15 to 20.

The size of each patch of the color chart is not particularly limited, and is preferably not too small from a viewpoint of not interfering with color recognition. In this regard, 0.25 $cm^2$ or more is preferable. In addition, from a viewpoint that the color chart is not too large, 4 $cm^2$ or less is preferable.

The shape of each patch includes, for example, a square.

The color chart preferably includes an automatic recognition marker for automatically recognizing at least one of the plurality of patches. Since the color chart includes the automatic recognition marker, it is possible to automatically perform an operation of recognizing each patch of the color chart in image data when the color correction to be described later is performed.

The shape and the size of the automatic recognition marker are not particularly limited, and are preferably, for example, the same as those of the patch. For example, the size of the automatic recognition marker is preferably 0.25 cm² or more and 4 cm² or less. In addition, the automatic recognition marker generally has a pattern that each patch does not have.

It is preferable that the color chart includes two or more automatic recognition markers having different patterns. When two or more automatic recognition markers are used, the automatic recognition for each patch is performed in consideration of relative positional relation between the two or more automatic recognition markers, and thus the automatic recognition performance for each patch is improved.

The automatic recognition marker is not particularly limited as long as it is a marker that enables the automatic recognition, and information such as version information of the color chart, a link to a use method, and an expiration date may be added to the automatic recognition marker by a two-dimensional barcode or the like. Further, the color chart may fade depending on a storage condition. In this regard, it may be preferable to set an expiration date for the color chart.

Here, an example of a method for automatically recognizing each patch of the color chart using the automatic recognition marker will be described.

First, the automatic recognition marker is detected from an image obtained by imaging the color chart. The detection of the automatic recognition marker can be performed using, for example, an image recognition device including general-purpose image recognition processing software. Specifically, pattern matching between an image of the automatic recognition marker stored in advance in the image recognition device and the image obtained by imaging the color chart is performed using the image recognition device, and thus the automatic recognition marker is detected from the image obtained by imaging the color chart.

Further, positional relation between the automatic recognition marker and each patch, in the color chart, is stored in advance in the image recognition device. For example, when two automatic recognition markers having different patterns are used, positional relation between each of the two automatic recognition markers and each patch is stored in advance in a storage unit of the image recognition device. Here, the image recognition device includes a combination of a CPU and a memory.

Then, by applying the stored positional relation to the color chart in the captured image, each patch of the color chart in the captured image can be automatically recognized using the detected automatic recognition marker.

The size of the color chart is not particularly limited, and from a viewpoint that the color chart can be held by one hand and the color chart does not become an obstacle even when the color chart is held near a face, the area of the color chart is preferably 40 cm² or more and 150 cm² or less.

The color chart is generally a sheet-shaped color chart. Further, the shape of a main surface of the color chart is, for example, a rectangle.

A material of the color chart is not particularly limited as long as each patch can be printed. For example, the color chart may be made of plastic resin (for example, synthetic paper) or may be made of paper.

The color chart preferably includes a blank portion at a lower right portion (a lower left portion when viewed from the front) of the main surface. Most humans are right-handed. Therefore, holding the blank portion of the color chart by a right hand makes it easier to naturally place the color chart on a right side of the face.

Here, an example of the color chart will be described with reference to drawings.

Figure 2:
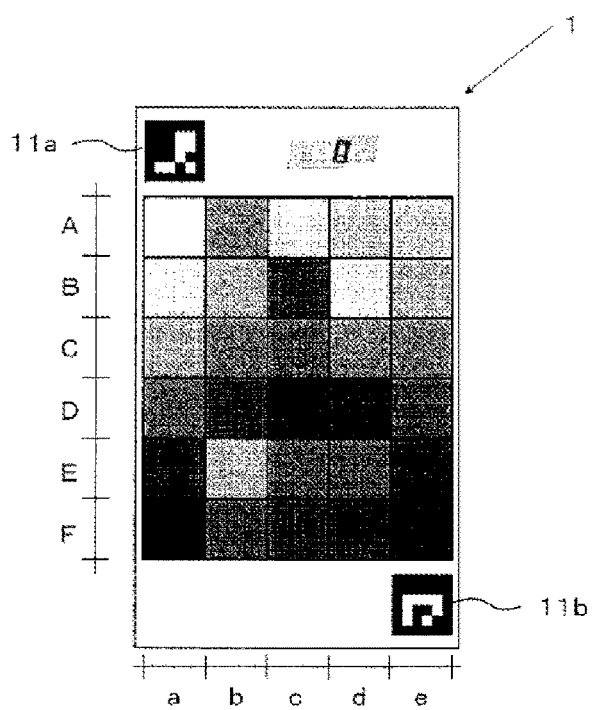
FIG. 2 is a schematic diagram of an example of a color chart.

FIG. 2 is a schematic diagram of an example of the color chart.

In addition, the color chart in FIG. 2 is a gray scale, but an actual color chart includes a chromatic color patch.

The color chart in FIG. 2 is a rectangle having a length of about 90 mm and a width of about 55 mm. Automatic recognition markers 11a and 11b of 10 mm square are disposed on an upper right portion (an upper left portion when viewed from the front) at an upper side and a lower left portion (a lower right portion when viewed from the front) at a lower side of a main surface of the color chart. The two automatic recognition markers 11a and 11b have white patterns on black backgrounds. The white pattern of the automatic recognition marker 11a is different from the white pattern of the automatic recognition marker 11b. In a central portion sandwiched between the upper side and the lower side, patches of 10 mm square are arranged without being spaced apart in 6 (A to F) rows and 5 (a to e) columns. In a rightmost column (first column: leftmost column when viewed from the front) of the main surface, achromatic color patches are arranged in order of brightness.

L*a*b* values of the patches of the color chart illustrated in FIG. 2 are illustrated in Table 1-1. In addition, outlines of colors of the patches of the color chart illustrated in FIG. 2 are illustrated in Table 1-2. In addition, relation between the first patch to the seventh patch and the skin color and the tongue color is illustrated in Table 1-3.

TABLE 1-1

|   | a | | | b | | | c | | | d | | | e | | |
|---|---|---|---|---|---|---|---|---|---|---|---|---|---|---|---|
|   | L* | a* | b* | L* | a* | b* | L* | a* | b* | L* | a* | b* | L* | a* | b* |
| A | 97 | 0 | 0 | 62 | 38 | 55 | 82 | 6 | 74 | 72 | 22 | 62 | 72 | 8 | 22 |
| B | 87 | 0 | 0 | 70 | −30 | −4 | 51 | −21 | −30 | 78 | 30 | 15 | 67 | 20 | 14 |
| C | 76 | 0 | 0 | 55 | 14 | −30 | 51 | 0 | −25 | 60 | 20 | 5 | 58 | 27 | 7 |
| D | 64 | 0 | 0 | 40 | 14 | −47 | 28 | 24 | −55 | 30 | 27 | −26 | 48 | 25 | 2 |
| E | 51 | 0 | 0 | 73 | −22 | 54 | 50 | 54 | −18 | 52 | 50 | 13 | 42 | 57 | 24 |
| F | 36 | 0 | 0 | 56 | −37 | 30 | 43 | −12 | 18 | 38 | 17 | 12 | 33 | 40 | 30 |

TABLE 1-2

| | a | b | c | d | e |
|---|---|---|---|---|---|
| A | White | Orange | Yellow | Pale orange | Dull yellow-red (first patch) |
| B | Very pale gray | Light gray-green | Sky blue | Pale red (second patch) | Pale yellow-red |
| C | Pale gray | Purple | Gray-blue | Purple-red (fourth patch) | Purple-red (third patch) |
| D | Gray | Purple-blue | Navy blue | Purple | Dull purple-red (fifth patch) |
| E | Deep gray | Yellow-green | Pink | Light red (sixth patch) | Red |
| F | Black | Green | Dark yellow-green | Dark yellow-red | Deep yellow-red (seventh patch) |

TABLE 1-3

| | a | b | c | d | e |
|---|---|---|---|---|---|
| A | | | | | A color of tongue coating formed due to accumulation of moisture (excess water) (first patch) |
| B | | | | A skin color that indicates an inflammation (second patch) | |
| C | | | | A color of a portion of a tongue covered with healthy tongue coating (fourth patch) | A color of a tongue having blood stasis (poor microcirculation) (third patch) |
| D | | | | | A color of deep lingual vein in an engorgement state = a blood stasis state (fifth patch) |
| E | | | | A color of healthy tongue (sixth patch) | |
| F | | | | | A color of a tongue having heat (seventh patch) |

<Imaging Device and Imaging Step>

The imaging device is a device that images a color chart and a person to be imaged simultaneously and acquires image data.

In the imaging step, the color chart and the person to be imaged are imaged simultaneously, and the image data is acquired.

The imaging step is performed by, for example, the imaging device.

The person to be imaged is, for example, a patient who is to receive a remote diagnosis and treatment.

The imaging devices includes, for example, a camera and an electronic device having a camera function.

The electronic device having the camera function includes, for example, a mobile phone, a smartphone, a tablet terminal, a personal computer, a monitoring camera, and a camera system attached to a medical examination apparatus (for example, a camera system attached to a f-MRI). In addition, a camera in the personal computer serving as the imaging device may be a built-in camera or an external camera.

An imaging element provided in the imaging device includes, for example, a charge coupled device (CCD) and a complementary metal oxide semiconductor (CMOS).

It is preferable that the imaging device includes, for example, a transmission unit that transmits the image data.

The transmission unit may transmit the image data by wireless communication, or wired communication.

As the wireless transmission, for example, wireless communication of any available type such as Wi-Fi, LTE, and 5G can be used.

The captured image may be a still image or a moving image.

<Display Device and Display Step>

The display device is a device that receives the image data and displays the image data on a display unit as an image. The display device includes at least the display unit, and further includes other units such as a color correction unit as necessary.

In the display step, the image data is received, and the image data is displayed on the display unit as an image.

In the display step, color correction processing may be further performed.

The display step is performed by, for example, the display device.

Figure 3:
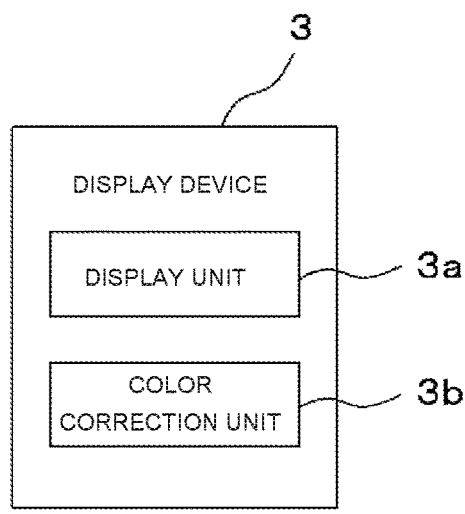
FIG. 3 is a functional configuration diagram of an example of a display device.

FIG. 3 illustrates a functional configuration diagram of an example of the display device. The display device 3 in FIG. 3 includes a display unit 3a and a color correction unit 3b.

The display device includes, for example, a reception unit that receives the image data.

For example, the image data is transmitted from the imaging device and received by the display device. The transmission and reception of the image data is generally performed through an Internet line.

The file format of the image data is not particularly limited, and may be any available format. For example, the file format of the image data includes JPG (JPEG), GIF, PNG, and BMP when the image data is a still image, and includes AVI, QuickTime, Mpeg-1, Mpeg-2, WMV, FLV, and MPEG-4 when the image data is a moving image.

The transmission and reception of the image data can be performed using, for example, a communication service such as an E-mail and a social networking service.

Further, when the image data is a moving image, for example, a web conference system such as Skype, Zoom, and Microsoft Teams may be used for the transmission and reception, and in addition to the image data, voice data may be transmitted and received.

As a method for transmitting the image data from the imaging device to the display device, a cloud may be used, the image data may be uploaded from the imaging device to the cloud server and the image data may be downloaded from the cloud server to the display device. That is, the display device may receive the image data from the cloud server.

Further, the method for transmitting the image data from the imaging device to the display device may be performed by physical movement via an external memory. For example, the display device can receive the image data by storing the image data acquired by the imaging device in an external memory such as a USB memory, physically moving the external memory by mail or the like, and then connecting the external memory to the display device.

Further, by storing the image data received a plurality of times in the display device, it is also possible to check a change over time of the person to be imaged using the image data.

The display unit is not particularly limited as long as it can display the image data, and the display unit include, for example, a color display.

The display device is not particularly limited, and the display device includes, for example, a mobile phone, a smartphone, a tablet terminal, a personal computer, and an output terminal of an electronic medical chart system.

<<Color Correction Unit and Color Correction Processing>>

The color correction unit is a unit that corrects a display color of the display unit and color information of the image data such that a color of at least one patch of a color chart in the image displayed on the display unit approaches or matches a color of at least one corresponding patch of a color chart measured under a light source at a place where the display unit is placed.

In color correction processing, the display color of the display unit and the color information of the image data are corrected such that the color of at least one patch of the color chart in the image displayed on the display unit approaches or matches the color of at least one corresponding patch of the color chart measured under the light source at the place where the display unit is placed.

The color correction processing is performed by, for example, the color correction unit.

The display device may include the color correction unit or may not include the color correction unit, but preferably includes the color correction unit.

The display step may include the color correction processing or may not include the color correction processing, but preferably includes the color correction processing.

The color correction unit is, for example, a CPU that executes a program for executing the color correction.

Here, the degree to which the colors are brought close to each other by the color correction may be appropriately selected according to a purpose.

Such color correction may be performed using only one of the patches in the color chart, or may be performed using a plurality of patches.

The color correction unit includes, for example, a first correction unit and a second correction unit.

The first correction unit is a unit that corrects the display color of the display unit such that a color of at least one patch of the color chart measured under the light source at the place where the display unit is placed and a corresponding display color of the display unit approach or match each other.

The second correction unit is a unit that corrects the color information of the image data such that a color of at least one patch of the color chart measured under the light source at the place where the display unit is placed and a color of at least one corresponding patch of the color chart in the image data approach or match each other.

The color correction processing includes, for example, first correction processing and second correction processing.

In the first correction processing, the display color of the display unit is corrected such that a color of at least one patch of the color chart measured under the light source at the place where the display unit is placed and a corresponding display color of the display unit approach or match each other.

In the second correction processing, the color information of the image data is corrected such that a color of at least one patch of the color chart measured under the light source at the place where the display unit is placed and a color of at least one corresponding patch of the color chart in the image data approach or match each other.

The first correction processing is performed by, for example, the first correction unit.

The second correction processing is performed by, for example, the second correction unit.

When the color chart and the person to be imaged are imaged simultaneously, the color information (for example, RGB values) in the obtained image data is different due to a difference in imaging environment, a difference in the type of the imaging device, or the like.

The difference in imaging environment includes, for example, a difference in the type of a light source for lighting and a difference in brightness of the lighting in a case of imaging indoors. Further, a difference in positional relation between the light source and an object to be imaged (a color chart and a person to be imaged) also affects the color information in the obtained image data.

The difference in the type of the imaging device includes, for example, a difference in the type of the imaging element and a difference in image processing engine. The image processing engine is, for example, a system LSI that processes a raw image output from the imaging element and converts the raw image into an image suitable for the humans to observe. The system LSI, which is the image processing engine, includes, for example, an embedded CPU, an embedded DSP, a dedicated arithmetic circuit that performs face detection and the like, a program memory, a data memory, and an image memory.

For example, in a case of color chart imaging, the color information of the patch of the color chart may be different in each obtained image data due to a difference in the type of the smartphone serving as the imaging device, a difference in the type of indoor lighting, or the like. Therefore, the color of the patch of the color chart in the image may vary even when the images are displayed on the same display unit. This difference may affect the remote diagnosis and treatment.

Further, a color of the patch of the color chart recognized by a person when a color chart is observed depends on an environment in which the color is observed (for example, the light source). This is because spectral distribution of light illuminating the color chart depends on the light source. Therefore, when the light sources are different, the color of the patch of the color chart recognized or measured when the color chart is observed varies. Therefore, even if the RGB values of the color of the patch of the color chart are accurately displayed on the display unit, the color of the patch of the color chart displayed on the display unit may be different from the color of the patch of the color chart recognized by the person under the light source at the place where the display unit is placed.

Therefore, the color correction unit and the color correction processing described above are useful.

Here, a specific example of the color correction in a case in which a doctor performs a remote diagnosis and treatment for a patient using the color chart will be described.

A purpose of the color correction is to match a color of a color chart (a color chart imaged together with a patient) in an image displayed on a display unit (for example, a display of a PC) used by the doctor to a color of a color chart at hand of the doctor, which is a correct value (a color of a color chart recognized by the doctor under a certain light source).

The color correction is performed in an order of color correction of a display color of the display used by the doctor (the first correction processing) and color correction of an image obtained by imaging the patient (the second correction processing).

First, an example of the first correction processing will be described.

In the first correction processing, the display color of the display unit is corrected such that a color of at least one patch of the color chart measured under the light source at the place where the display unit is placed and a corresponding display color of the display unit approach or match each other.

Specifically, first, the color of at least one patch of the color chart measured under the light source at the place where the display unit is placed is measured. Then, the display color of the display is corrected to approach or match the measured color.

The person recognizes the color by tristimulus values XYZ. Therefore, XYZ values, which are correct values, are measured and obtained by a colorimeter under the same lighting environment as a lighting environment of the doctor. As the colorimeter, for example, a Konica Minolta color luminance meter CS-100A is used.

Correction for the display is specifically performed as follows with reference to the following non patent literature.

Matsushita, F., Kiyomitsu, K., Ogawa, K., & Tsumura, N. (2019). Evaluation of Kampo disease states using facial images. Artificial Life and Robotics, 24(1), pp. 44-51

Relation between luminances and input RGB levels is expressed by the following Equation (1).

[Math. 1]

$$L'_R = a_0 R^2 + a_1 R + a_2$$

$$L'_G = b_0 G^2 + b_1 G + b_2$$

$$L'_B = c_0 B^2 + c_1 B + c_2 \quad (1)$$

Here, $L'_R$, $L'_G$, and $L'_B$ are luminances of red, green, and blue, respectively, and $a_i$, $b_i$, and $c_i$ (i=0, 1, 2) are coefficients.

Tristimulus values X', Y', and Z' of the display color of the display can be decomposed into contributions of R, G, and B as indicated in the following Equation (2).

[Math. 2]

$$\begin{pmatrix} X' \\ Y' \\ Z' \end{pmatrix} = \begin{pmatrix} X'_R + X'_G + X'_B \\ Y'_R + Y'_G + Y'_B \\ Z'_R + Z'_G + Z'_B \end{pmatrix} \quad (2)$$

Here, $X'_i$, $Y'_i$, and $Z'_i$ (i=R, G, B) indicate tristimulus values for red emission, green emission, and blue emission, respectively. The tristimulus values corresponding to the emission can be calculated based on luminance L and color coordinates x and y when the display is measured. Relation of X-Y and Y-Z for each emission can be expressed by a linear equation represented by the following Equation (3).

[Math. 3]

$$X'_R = a_R Y'_R + b_R$$

$$X'_G = a_G Y'_G + b_G$$

$$X'_B = a_B Y'_B + b_B$$

$$Z'_R = c_R Y'_R + d_R$$

$$Z'_G = c_G Y'_G + d_G$$

$$Z'_B = c_B Y'_B + d_B \quad (3)$$

Here, $a_i$, $b_i$, $c_i$, and $d_i$ (i=R, G, B) are coefficients.

From Equation (2) and Equation (3), the following Equation (4) is obtained.

[Math. 4]

$$\begin{pmatrix} X' \\ Y' \\ Z' \end{pmatrix} = \begin{pmatrix} a_R Y'_R + a_G Y'_G + a_B Y'_B + b_R + b_G + b_B \\ Y'_R + Y'_G + Y'_B \\ c_R Y'_R + c_G Y'_G + c_B Y'_B + d_R + d_G + d_B \end{pmatrix}$$

$$= A \begin{pmatrix} Y'_R \\ Y'_G \\ Y'_B \end{pmatrix} + \begin{pmatrix} b_R + b_G + b_B \\ 0 \\ d_R + d_G + d_B \end{pmatrix}$$

$$A = \begin{pmatrix} a_R & a_G & a_B \\ 1.0 & 1.0 & 1.0 \\ c_R & c_G & c_B \end{pmatrix} \quad (4)$$

Based on Equation (4), luminances of the RGB when certain tristimulus values X'Y'Z' are desired to be displayed on the display can be obtained by Equation (5).

[Math. 5]

$$\begin{pmatrix} L'_R \\ L'_G \\ L'_B \end{pmatrix} = \begin{pmatrix} Y'_R \\ Y'_G \\ Y'_B \end{pmatrix} = A^{-1} \begin{pmatrix} X' - b_R - b_G - b_B \\ Y' \\ Z' - d_R - d_G - d_B \end{pmatrix} \quad (5)$$

The XYZ values of the patch of the color chart, which are the correct values measured by the colorimeter under the same lighting environment as the lighting environment of the doctor, are entered into X', Y', and Z' in Equation (5). Then, by applying the luminances obtained based on Equation (5) into Equation (1), RGB values (reference RGB values) can be calculated. Then, the display color (RGB values) of the display corresponding to the color (RGB values) of the patch of the color chart is corrected to the calculated RGB values (reference RGB values). Accordingly, the display color of the display used by the doctor can be corrected. That is, according to the above procedure, the display color of the display can be corrected to the correct values.

Next, an example of the second correction processing will be described.

In the second correction processing, the color information of the image data is corrected such that a color of at least one patch of the color chart measured under the light source at the place where the display unit is placed and a color of at least one corresponding patch of the color chart in the image data approach or match each other.

Specifically, RGB values of at least one patch of the color chart in the image data of the image obtained by imaging the color chart and the patient are corrected to the corresponding reference RGB values calculated in the first processing correction.

More specifically, each portion of patch of the color chart is extracted from the captured image using the automatic recognition marker, and average values of RGB values of pixels in a patch is obtained for each patch. A model is created by multiple regression based on a difference between the averaged numbers (RGB values) and the corresponding reference RGB values. Based on the model, all pixels of the image data are converted, and a color of a face, a tongue, or the like of an imaged person is corrected.

The correction is performed by examining correlation between the RGB values of the patch of the color chart in the image data of the image obtained by imaging the patient and the corresponding reference RGB values.

In the correction, first, gamma correction of the image data is performed using achromatic colors in the patches of the color chart of the captured image. Then, the RGB values of the image data are corrected using all chromatic colors in the patches of the color chart.

The gamma correction will be described in detail. First, in the first correction processing, the gamma correction is performed, based on luminances when achromatic color portions in the patches of the color chart are measured by the colorimeter, on RGB values of the achromatic color portions in the captured image. Similarly, the gamma correction is also performed for a gray scale portion of the reference RGB values.

Then, the gamma correction is performed for each of the RGB values. The R value is as illustrated in Equation (6).

[Math. 6]

$$R_c = aY^\gamma + b \quad (6)$$

$R_c$ is an R value of the captured image, and Y is a luminance obtained when the achromatic color in the patch of the color chart is measured by the colorimeter. Normalization is performed with a luminance value of white such that black is 0 and white is 1 among the achromatic colors of the color chart, and thus brightness of the achromatic color is converted into a range of 0 to 1. By this model, the gamma correction is performed for any of the RGB values. Specifically, RGB values obtained after the gamma correction are calculated by multiplying the RGB values by an inverse function of Equation (6).

Then, a model is constructed by the multiple regression for the color of the patch for which the gamma correction is performed. The R value is as illustrated in Equation (7).

[Math. 7]

$$R'_c = aR_r + bG_r + cB_r + d \quad (7)$$

$R'_c$ is a R value of the corrected image, and $R_r$, $G_r$, and $B_r$ are RGB values before correction. Each parameter (a, b, c, d) is obtained by the multiple regression using the corresponding patch.

An example of the image display method using the image display system will be described with reference to the drawings.

Figure 4:
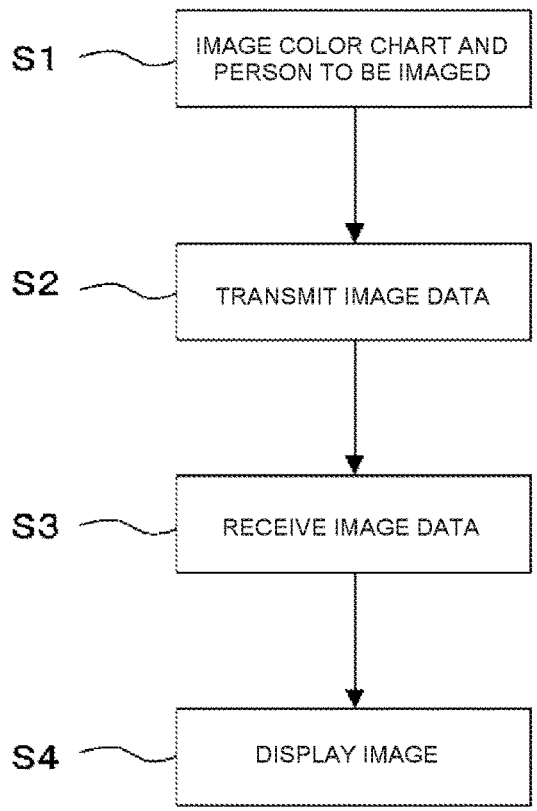
FIG. 4 is a flowchart of an example of an image display method.

FIG. 4 is a flowchart of an example of the image display method.

Figure 5:
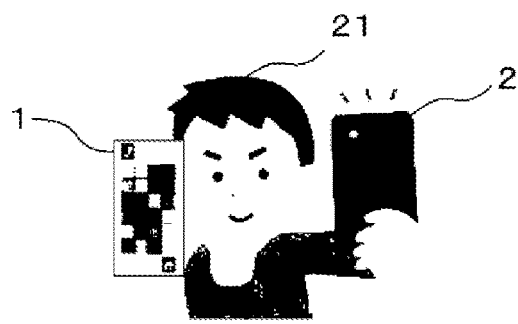
FIG. 5 is a schematic diagram of an example in which the color chart and a patient are imaged simultaneously by an imaging device.

First, as illustrated in FIG. 5, the color chart 1 and a person to be imaged 21 are imaged simultaneously using a smartphone that is the imaging device 2 (S1).

Then, image data obtained by the imaging is transmitted from the imaging device 2 to the display device 3 (S2).

Then, the image data transmitted from the imaging device 2 is received by the display device 3 (S3). The image data is transmitted and received by, for example, being attached to an e-mail.

Figure 6:
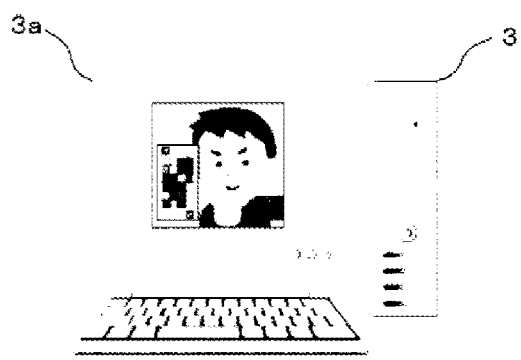
FIG. 6 is a schematic diagram of an example in which a captured image is displayed on a display unit of the display device.

Finally, as illustrated in FIG. 6, the image data is displayed as an image on the display unit 3a (display) of a PC that is the display device 3 (S4).

As described above, the example of the image display method is performed.

Figure 7:
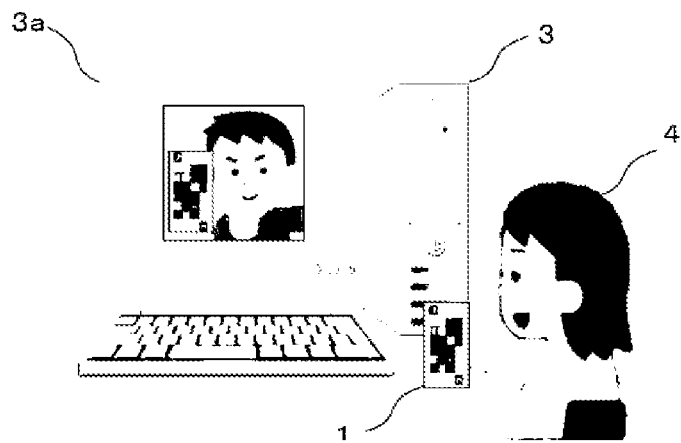
FIG. 7 is a schematic diagram of an example in which a doctor displays the captured image on the display unit of the display device to perform remote diagnosis and treatment.

Further, when the remote diagnosis and treatment using the image display method is performed, as illustrated in FIG. 7, a doctor 4, who is a diagnostician, observes a skin color of a face and a tongue color of the patient, who is the person to be imaged 21, displayed on the display unit 3a while holding the same color chart 1 as the color chart 1 held by the patient and considering a difference between a color of the color chart 1 displayed on the display unit 3a and a color of the color chart 1 held by the doctor 4, and performs a diagnosis.

Another example of the image display method using the image display system will be described with reference to the drawings.

Figure 8:
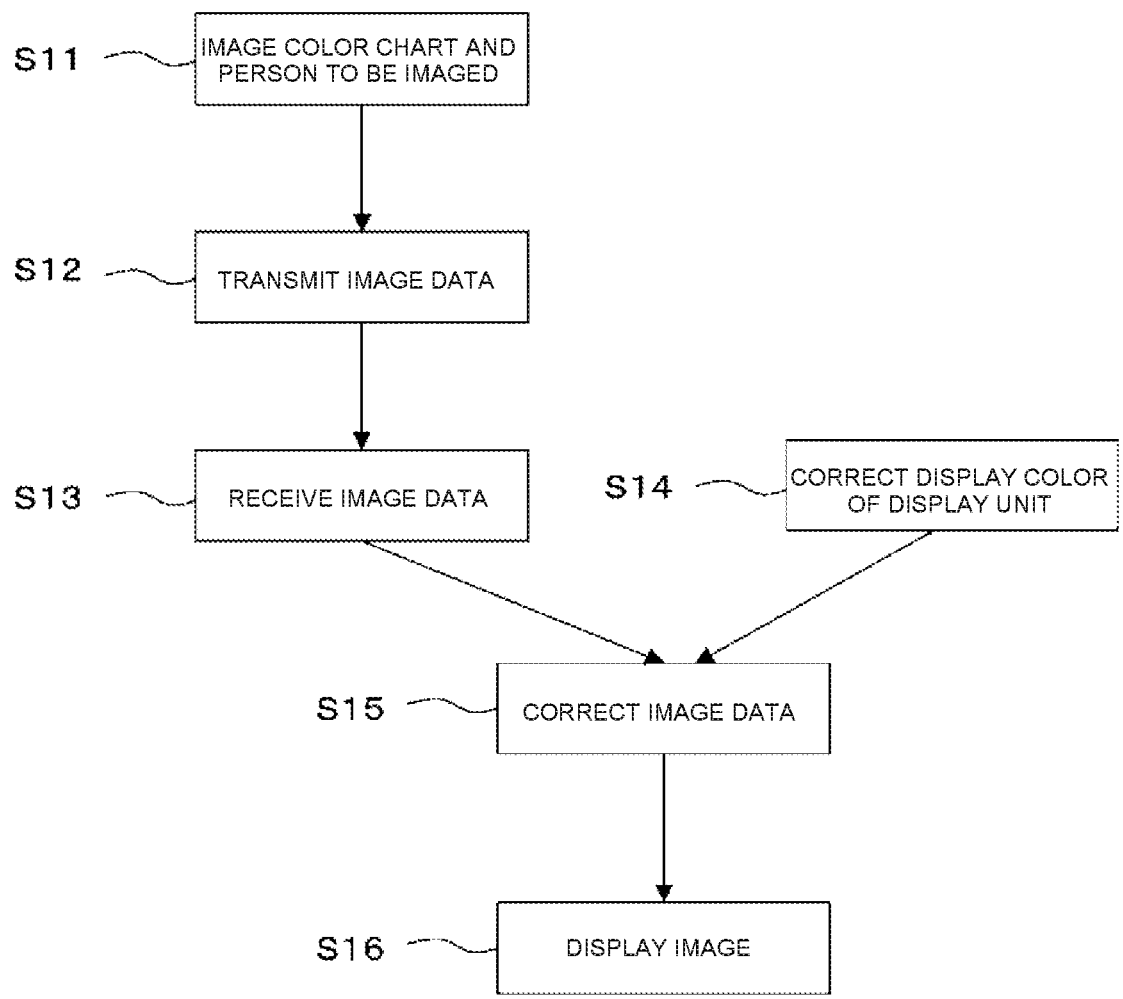
FIG. 8 is a flowchart of another example of the image display method.

FIG. 8 is a flowchart of another example of the image display method.

First, as illustrated in FIG. 5, the color chart 1 and the person to be imaged 21 are imaged simultaneously using a smartphone that is the imaging device 2 (S11).

Then, image data obtained by the imaging is transmitted from the imaging device 2 to the display device 3 (S12).

Then, the image data transmitted from the imaging device 2 is received by the display device 3 (S13). The image data is transmitted and received by, for example, being attached to an e-mail.

On the other hand, a display color of the display unit 3a is corrected (S14). Specifically, the display color of the display unit is corrected such that a color of at least one patch of the color chart measured under the light source at the place where the display unit is placed and a corresponding display color of the display unit approach or match each other. The color correction is performed by the color correction unit 3b.

Then, the image data is corrected (S15). Specifically, the color information of the image data is corrected such that a color of at least one patch of the color chart measured under the light source at the place where the display unit is placed and a color of at least one corresponding patch of the color chart in the image data approach or match each other (S15). The color correction is performed by the color correction unit 3b. When the color correction is performed, each patch of the color chart in the image is automatically recognized using the automatic recognition marker.

Finally, as illustrated in FIG. 6, the corrected image data is displayed as an image on the display unit 3a (display) of the PC that is the display device 3 (S16).

As described above, the example of the image display method is performed. In addition, the step S14 does not have to be performed after the step S13, and the step S14 and other steps may be performed in any order.

Further, when remote diagnosis and treatment using the image display method is performed, as illustrated in FIG. 7, the doctor 4, who is a diagnostician, observes a skin color of a face and a tongue color of the patient displayed on the display unit 3a while holding the same color chart 1 as the color chart 1 held by the patient who is the person to be imaged 21, and performs a diagnosis.

In this example, since the color correction is performed, as compared with a case in which the color correction is not performed, the skin color of the face of the patient in the image is close to the skin color of the face of the patient observed when it is assumed that the face-to-face diagnosis and treatment is performed. Therefore, when inspecting the skin color and the tongue color of the patient, the doctor can perform the remote diagnosis and treatment in a state close to a state in which the face-to-face diagnosis and treatment is performed.

EMBODIMENT

Hereinafter, the invention will be described in more detail with reference to embodiments, but the scope of the invention is not limited to these embodiments.

First Embodiment

Image display and a simulation diagnosis in the remote diagnosis and treatment were performed according to the flowchart illustrated in FIG. 4.

As a color chart, the color chart illustrated in FIG. 2 was used.

The simulation diagnosis in the remote diagnosis and treatment was performed by eight doctors from the Department of Kampo Medicine at the Kanazawa University Hospital.

First, the patient was imaged using the camera function of the smartphone such that both the face of the patient and the color chart are imaged. The photographic image obtained by the imaging was attached to an e-mail and sent to the doctors. The doctor who received the e-mail displayed the photographic image on the display of the PC. The doctor compared an actual color chart on hand with the color chart imaged in the photographic image, and judged the skin color of the face of the patient with sense of the doctors in consideration of a difference between the color charts. Further, for doctors who are not familiar with color comparison, a procedure manual described below is given to the doctors in advance. In the following procedure manual, "left side" means the left side when viewed from the front.

[Procedure Manual]

(1) Grayscale: Observe a shade portion from black to white on the left side of the color chart and observe a difference in brightness levels.

(2) Look at red patches and observe the intensity of red. In this way, a difference in appearance of the complexion is taken into consideration.

(3) Look at the patch of a healthy tongue color and observe the shade of the color.

(4) Look at blue patches and observe the intensity of the color. In this way, differences in the intensity of red and blue are determined.

(5) A state of the patient is more accurately grasped by the tongue and skin color patch.

(6) A patch having a color of dermatitis is also prepared, which can be used to identify inflammation.

Evaluation comments of the eight doctors who are the judges were illustrated in Table 2. Doctors having color knowledge gave good ratings. Doctors having little knowledge of color found utility value based on description on how to use the color chart. There were no negative comments, and evaluation was that better diagnosis and treatment can be performed than when the color chart was not used.

TABLE 2

| Judge No. | comment |
|---|---|
| 1 | I though it is great to prepare a color chart, so we can make corrections based on a model and lighting. Since it is |

TABLE 2-continued

| Judge No. | comment |
|---|---|
|  | difficult to make a diagnosis based on a video, it would be better to send several still images to make a diagnosis. |
| 2 | Once I got used to the color chart, I can well understand how to use it. |
| 3 | I felt that the color chart has the potential to lead to objective diagnosis. |
| 4 | I felt that it was difficult to judge whether it was a shadow unless the light was applied from the front of the tongue. If possible, it would be better to have images taken from three directions, such as the front, the first oblique, and the second oblique, so that we could make a more reliable diagnosis. But, it just gets complicated. |
| 5 | I think this proposal is good because people who are unfamiliar with the tongue color can easily get a subjective impression of the color. |
| 6 | It can be useful for the remote diagnosis and treatment. I would like to get used to using the color chart with my patients as soon as possible. |
| 7 | I didn't know what I was looking at before, but this chart may help me figure it out. |
| 8 | Accurate diagnosis can be made by capturing images of skin diseases before and after treatment and over time with a color checker. |

Second Embodiment

The image display was performed according to the flowchart illustrated in FIG. 8.

As a color chart, the color chart illustrated in FIG. 2 was used.

The color correction of the image was performed by the method described above using Equations (1) to (7).

The program for executing the color correction was created by Python.

As a result, the skin color of the face of the patient in the image displayed on the display unit was similar to the skin color of the face observed when it was assumed that the face-to-face diagnosis and treatment was performed.

A doctor of Chinese medicine evaluated the image displayed on the display unit. In the evaluation result, an opinion was obtained that the color correction within a reliable range was performed in the diagnosis and treatment.

REFERENCE SIGNS LIST

1: Color chart
2: Imaging device
3: Display device
3*a*: Display unit
4: Doctor
11*a*, 11*b*: Automatic recognition marker
21: Person to be imaged

The invention claimed is:

1. An image display system comprising:
a color chart including a plurality of patches that include at least three patches selected from a group consisting of the following first to seventh patches;
an imaging device configured to simultaneously image the color chart and a person to be imaged and acquire image data; and
a display device configured to receive the image data and display the image data as an image on a display unit thereof,
wherein
the first patch includes a region that has a first color represented by $L^*a^*b^*$ values in which $L^*=72$, a*=8, and b*=22 or has a color having a color difference ΔE* of 5 or less in a L*a*b* color space with respect to the first color,
the second patch includes a region that has a second color represented by the L*a*b* values in which L*=78, a*=30, and b*=15 or has a color having a color difference ΔE* of 5 or less in the L*a*b* color space with respect to the second color,
the third patch includes a region that has a third color represented by the L*a*b* values in which L*=58, a*=27, and b*=7 or has a color having a color difference ΔE* of 5 or less in the L*a*b* color space with respect to the third color,
the fourth patch includes a region that has a fourth color represented by the L*a*b values in which L*=60, a*=20, and b*=5 or has a color having a color difference ΔE* of 5 or less in the L*a*b* color space with respect to the fourth color,
the fifth patch includes a region that has a fifth color represented by the L*a*b* values in which L*=48, a*=25, and b*=2 or has a color having a color difference ΔE* of 5 or less in the L*a*b* color space with respect to the fifth color,
the sixth patch includes a region that has a sixth color represented by the L*a*b* values in which L*=52, a*=50, and b*=13 or has a color having a color difference ΔE* of 5 or less in the L*a*b* color space with respect to the sixth color, and
the seventh patch includes a region that has a seventh color represented by the L*a*b* values in which L*=33, a*=40, and b*=30 or has a color having a color difference ΔE* of 5 or less in the L*a*b* color space with respect to the seventh color.

2. The image display system according to claim 1, wherein the plurality of patches include a plurality of achromatic color patches having different brightness.

3. The image display system according to claim 1, wherein the plurality of patches include a plurality of chromatic color patches whose colors are different from the first color to the seventh color.

4. The image display system according to claim 1, wherein the color chart has an area of 40 cm² or more and 150 cm² or less.

5. The image display system according to claim 1, wherein each of the plurality of patches has an area of 0.25 cm² or more and 4 cm² or less.

6. The image display system according to claim 1, wherein the color chart includes an automatic recognition marker for automatically recognizing at least one of the plurality of patches.

7. The image display system according to claim 1, wherein the color chart has a blank portion at a lower right portion on a main surface thereof.

8. The image display system according to claim 1, wherein the imaging device is an electronic device having a camera function.

9. The image display system according to claim 1, wherein the display device is a personal computer.

10. The image display system according to claim 1, wherein the display device further includes a color correction unit configured to correct a display color of the display unit and color information of the image data such that a color of at least one patch of the color chart in the image displayed on the display unit approaches or matches a color of at least one corresponding patch of a color chart measured under a light source at a place where the display unit is placed.

11. The image display system according to claim 10, wherein
the color correction unit includes
a first correction unit configured to correct the display color of the display unit such that a color of at least one patch of the color chart measured under the light source at the place where the display unit is placed and a corresponding display color of the display unit approach or match each other, and
a second correction unit configured to correct the color information of the image data such that a color of at least one patch of the color chart measured under the light source at the place where the display unit is placed and a color of at least one corresponding patch of the color chart in the image data approach or match each other.

12. An image display method comprising:
simultaneously imaging a color chart including a plurality of patches that include at least three patches selected from a group consisting of the following first to seventh patches, and a person to be imaged, and acquiring image data; and
receiving the image data and displaying the image data as an image on a display unit,
wherein
the first patch includes a region that has a first color represented by L*a*b* values in which L*=72, a*=8, and b*=22 or has a color having a color difference ΔE* of 5 or less in a L*a*b* color space with respect to the first color,
the second patch includes a region that has a second color represented by the L*a*b* values in which L*=78, a*=30, and b*=15 or has a color having a color difference ΔE* of 5 or less in the L*a*b* color space with respect to the second color,
the third patch includes a region that has a third color represented by the L*a*b* values in which L*=58, a*=27, and b*=7 or has a color having a color difference ΔE* of 5 or less in the L*a*b* color space with respect to the third color,
the fourth patch includes a region that has a fourth color represented by the L*a*b values in which L*=60, a*=20, and b*=5 or has a color having a color difference ΔE* of 5 or less in the L*a*b* color space with respect to the fourth color,
the fifth patch includes a region that has a fifth color represented by the L*a*b*values in which L*=48, a=25, and b*=2 or has a color having a color difference ΔE" of 5 or less in the L*a"b" color space with respect to the fifth color,
the sixth patch includes a region that has a sixth color represented by the L*a*b* values in which L*=52, a*=50, and b=13 or has a color having a color difference ΔE* of 5 or less in the L*a"b" color space with respect to the sixth color, and
the seventh patch includes a region that has a seventh color represented by the L*a"b" values in which L*=33, a*=40, and b*=30 or has a color having a color difference ΔE* of 5 or less in the L*a"b" color space with respect to the seventh color.

* * * * *